(12) United States Patent  (10) Patent No.: US 7,448,243 B1
Motsenbocker  (45) Date of Patent: Nov. 11, 2008

(54) SWAGING TECHNOLOGY

(75) Inventor: Thomas Motsenbocker, Flagstaff, AZ (US)

(73) Assignee: Machine Solutions, Inc., Flagstaff, AZ (US)

( * ) Notice: Subject to any disclaimer, the term of this patent is extended or adjusted under 35 U.S.C. 154(b) by 59 days.

(21) Appl. No.: 11/406,118

(22) Filed: Apr. 17, 2006

Related U.S. Application Data

(60) Provisional application No. 60/671,909, filed on Apr. 15, 2005.

(51) Int. Cl.
  *B21J 7/16* (2006.01)
(52) U.S. Cl. ............................................. 72/76; 72/402
(58) Field of Classification Search .................. 72/402, 72/76; 29/237, 282, 283.5
  See application file for complete search history.

(56) References Cited

U.S. PATENT DOCUMENTS

| | | | | |
|---|---|---|---|---|
| 474,548 | A | * | 5/1892 | Dayton ............................ 72/76 |
| 1,894,800 | A | * | 1/1933 | Stowe ............................. 72/76 |
| 2,381,559 | A | * | 8/1945 | Root .............................. 72/76 |
| 3,273,367 | A | * | 9/1966 | Hallden ......................... 72/76 |
| 4,455,851 | A | * | 6/1984 | Kienhofer ...................... 72/76 |
| 4,464,917 | A | * | 8/1984 | Kienhofer ...................... 72/76 |

* cited by examiner

*Primary Examiner*—Daniel C Crane
(74) *Attorney, Agent, or Firm*—Skinner and Associates

(57) ABSTRACT

A swager for swaging articles, such as marker bands to a medical catheter, comprising an article input mechanism; a radial compression swaging head with a central swaging aperture, the swaging head being aligned and communicatively coupled with the input mechanism to receive an input article from the article input mechanism and to swage the article. The swaging head includes a plurality of swage elements; a rotatable slider plate; a plurality of track rollers; and a closer plate. An input mechanism is aligned and communicatively coupled with the swaging head to assist in delivering an article to the swaging head.

19 Claims, 23 Drawing Sheets

SWAGING TECHNOLOGY

CROSS-REFERENCE TO RELATED APPLICATIONS, IF ANY

This application claims the benefit under 35 U.S.C. § 119(e) of U.S. Provisional Patent Application Ser. No. 60/671,909, filed Apr. 15, 2005, which is hereby incorporated by reference.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND

1. Field

The present invention relates, generally, to material forming systems, apparatus and processes. More particularly, the invention relates to a swaging system, apparatus and method. Most particularly, the invention relates to a system, apparatus and method for swaging one or more articles such as marker bands at precise locations on a tubular structure such as a medical catheter. The techniques of the invention can also be used in other fields such as tube joining, cable joining, sealing, bullet manufacturing, and other medical, industrial, commercial apparatus and processes.

2. Background Information

Swaging is a forming process for use with hollow or solid material or articles, particularly metallic material or articles. Examples of hollow material or articles include tubes, casings, catheters, needles and the like. Examples of solid materials include rods, bars and wires. Swaging is commonly used to reduce or increase the diameter of material or articles, to create particular geometric shapes or profiles of material or articles, to join or fasten material or articles, or to seal or finish material or articles. Swaging is typically accomplished by placing material or articles, most commonly tubes, rods, bars or wires, inside a die that applies compressive force. Typically, the force is applied by radially hammering. The radial hammering may be accompanied by rotating the die or the workpiece. Additionally, a mandrel may be placed inside articles such as tubes during compression. The inner and outer diameters of the material or articles may be of the same or differing shapes. Swaging is typically conducted cold, or at room temperature, but may be conducted hot. Swaging may be accomplished by a rotary process, a stationary spindle process, or a die closing process. Other known forming processes include crimping and pointing.

Examples of existing swaging technology includes a rotary swager provided by Torrington Swaging and Vaill End Forming Machinery, Inc. of Waterbury, Conn. The rotary swager has a motorized spindle which is slotted, in order to hold backers and the dies. The spindle passes the backers over the rollers to deliver a blow to the dies. In this rotary swaging process, a swaging head is fixed. The dies close over a work piece and form the material. When the backers are in-between two roll positions, the centrifugal forces will move them apart, making it possible for the die to open, while the dies are rotating around the workpiece. The operation continues several times and the result is a reduced round cross section of tube, bar or wire.

Marker band swaging equipment is also manufactured and sold by applicants' assignee, Machine Solutions, Inc. of Flagstaff, Ariz., USA under model numbers SW100S, SW300S, SW500S and SW1100S. This technology is further disclosed in US Patent Application No US2004/0096538A1 to Edward Goff and Tom Motsenbocker, published May 20, 2004, now U.S. Pat. No. 6,931,899 issued, Aug. 23, 2005.

A stationary spindle swager, also provided by Torrington Swager has a spindle and dies which are fixed. They do not rotate around the workpiece. Instead, the head rotates. This type of machine is used to obtain cross-sectioned shapes other than round, such as triangular, square, polygonal.

A die closing swage, further provided by Torrington Swager has dies which are moved radially by a die closing device and by backers while the operation is being performed. A spindle is motorized and rotating. This type of machine is used to obtain grooves or recesses for short step transition angles or for assembly of large parts on cables or rods without having to remove the dies between operations.

Numerous medical devices exist for accessing and working within the vasculature and other internal systems of humans and other animals for minimally invasive diagnostic and therapeutic purposes. Examples of such devices include introducers, guidewires, catheters, and stents. They are typically thin, elongated structures which are inserted into arteries, veins, or body cavities through small punctures in the skin. After initial insertion, the insertable medical devices, and in particular certain portions or aspects of the devices such as balloons, blades, tips, drug delivery systems, are guided to desired locations in the body, such as the heart or other organs, by radioscopic or flouroscopic visualization. In such visualization processes, a medical practitioner views the medical device or a portion thereof in the body through a screen or other monitoring device. Visualization is enhanced or even made possible by a radiopaque marker, typically a band or series of bands of a predetermined geometry and disposed at a predetermined position(s) on the insertable medical device or portion thereof. Marker bands have been placed on insertable medical devices by existing swaging devices and processes.

BRIEF SUMMARY OF THE INVENTION

The present invention provides a swaging system, apparatus and method which are practical, reliable, accurate and efficient, and which are believed to fulfill a need and to constitute an improvement over the background technology.

The swaging system, apparatus and process is useful for swaging metal bands to polymeric tubular structures in a precise, substantially automated fashion. In particular, the swaging system, apparatus and process is beneficial for swaging marker bands to medical catheters, guidewires, stents and the like. In general however, the swaging system, apparatus and process may be used for forming or processing hollow or solid material or articles, particularly those constructed of malleable metals, such as tubes, casings, catheters, needles, rods, bars and wires, to reduce or increase the diameter, to create particular geometric shapes or profiles, to join or fasten, or to seal or finish such material or articles.

In one aspect the invention provides a swage head comprising a first plate, a second plate rotatable with respect to the first plate, a plurality of swage elements slidably coupled to the second plate and having a swaging profile adapted to contact a product to be swaged and a cam profile, and a plurality of slide rollers rotatably connected to the first plate and adapted to contact the cam profile of the swage elements.

In another aspect the invention provides a swaging assembly, comprising:
  a. a swage head comprising a first plate, a second plate rotatable with respect to the first plate, a plurality of swage elements slidably coupled to the second plate and having a swaging profile adapted to contact a product to be swaged and a cam profile, and a plurality of slide rollers rotatably connected to the first plate and adapted to contact the cam profile of the swage elements;
  b. a mount supporting the swage head; and
  c. a drive actuating the swage head and rotating the second plate.

And in a further aspect the invention provides swaging system for swaging an article, comprising:
  a. a swaging assembly, comprising:
    i. a swage head comprising a first plate, a second plate rotatable with respect to the first plate, a plurality of swage elements slidably coupled to the second plate and having a swaging profile adapted to contact a product to be swaged and a cam profile, and a plurality of slide rollers rotatably connected to the first plate and adapted to contact the cam profile of the swage elements;
    ii. a mount supporting the swage head; and
    iii. a drive actuating the swage head and rotating the second plate; and
  b. an article input assembly for orienting an article for swaging with respect to the swaging assembly.

The features, benefits and objects of the invention will become clear to those skilled in the art by reference to the following description, claims, and drawings.

DETAILED DESCRIPTION

Figure 1:
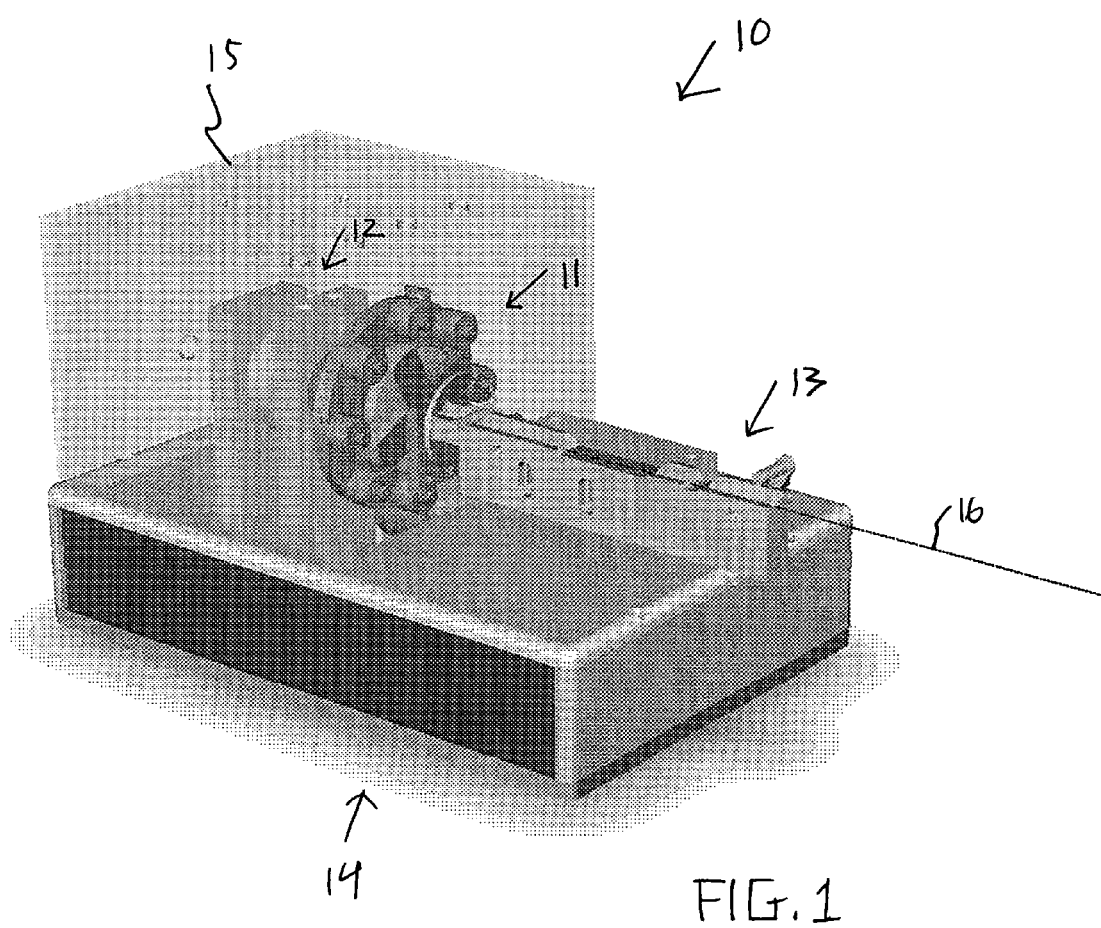
FIG. 1 is a perspective view of an embodiment of the swaging system of the present invention.
Figure 2:
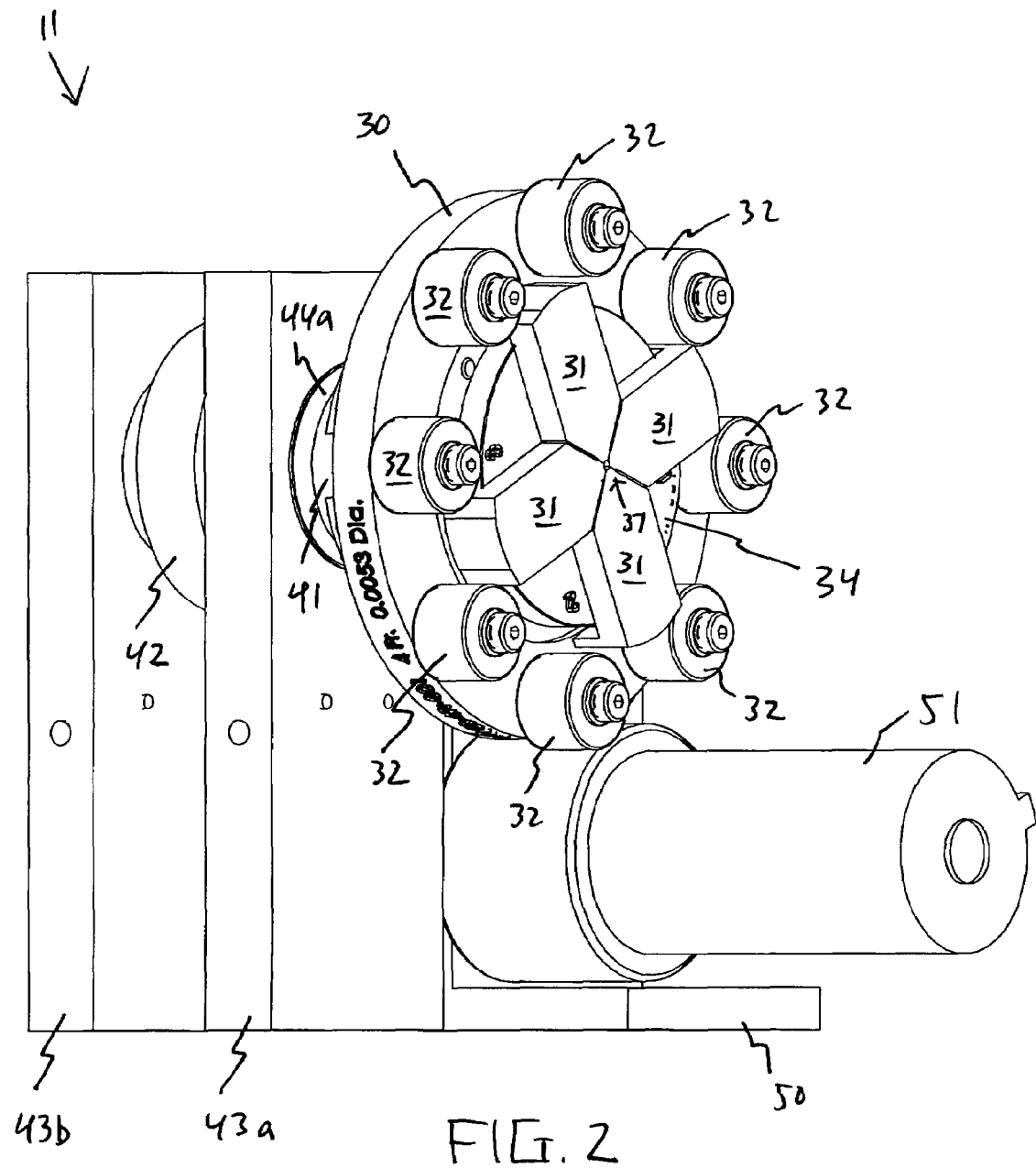
FIG. 2 is a perspective view from the front left side of an embodiment of a swaging assembly used in the swaging system.
Figure 3:
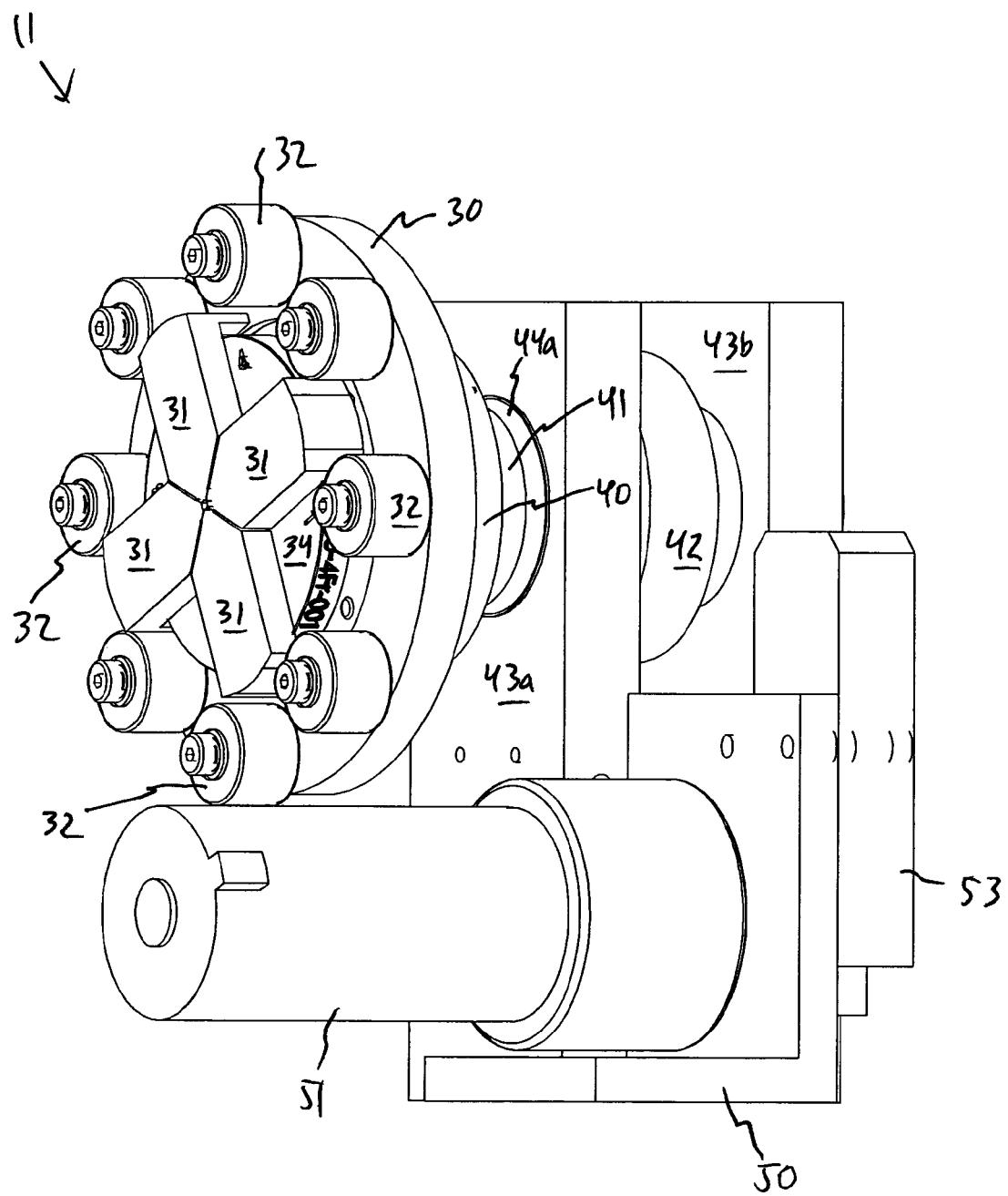
FIG. 3 is a perspective view from the front right side of the swaging assembly.
Figure 4:
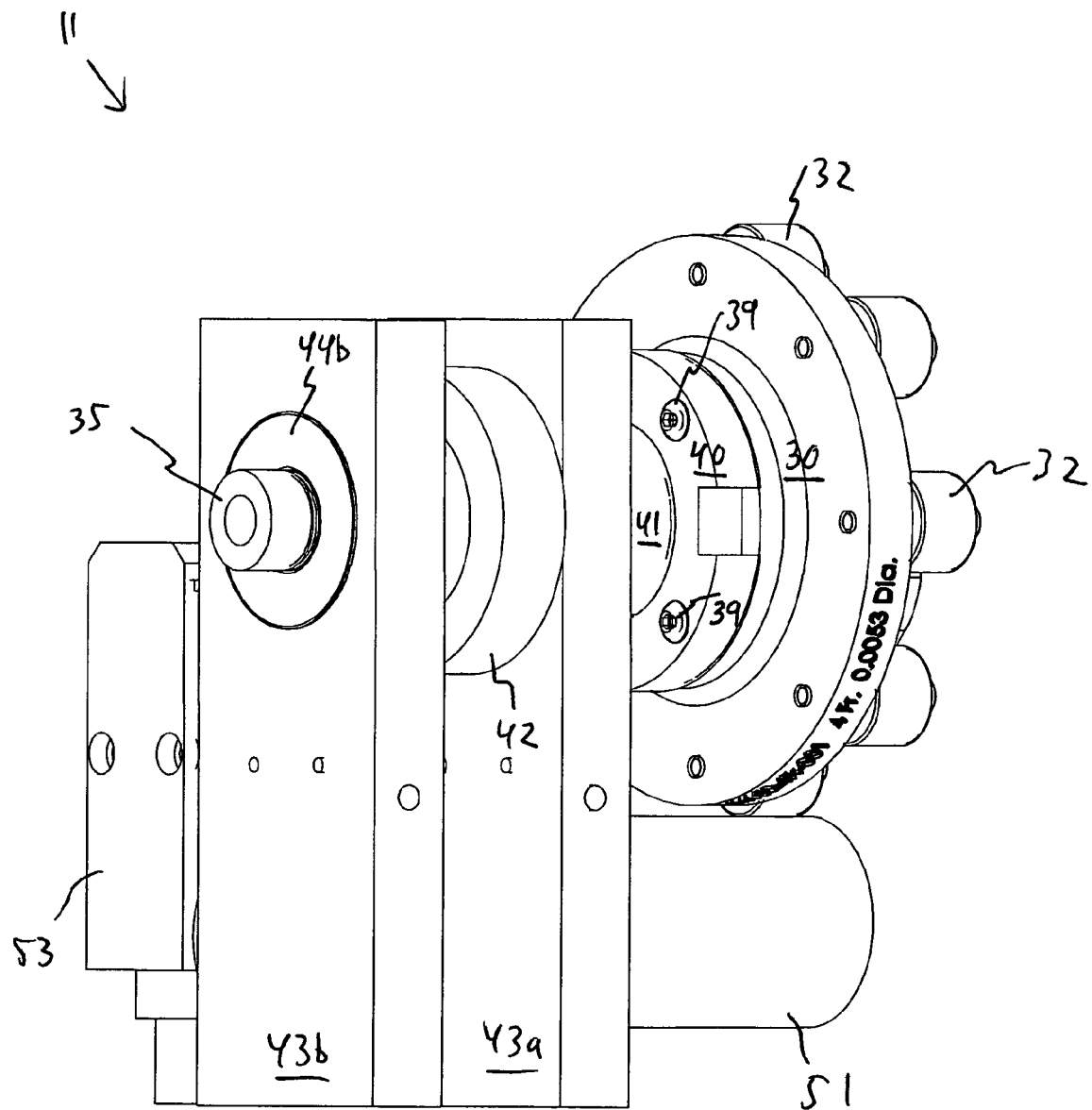
FIG. 4 is a perspective view from the rear left side of the swaging assembly.
Figure 5:
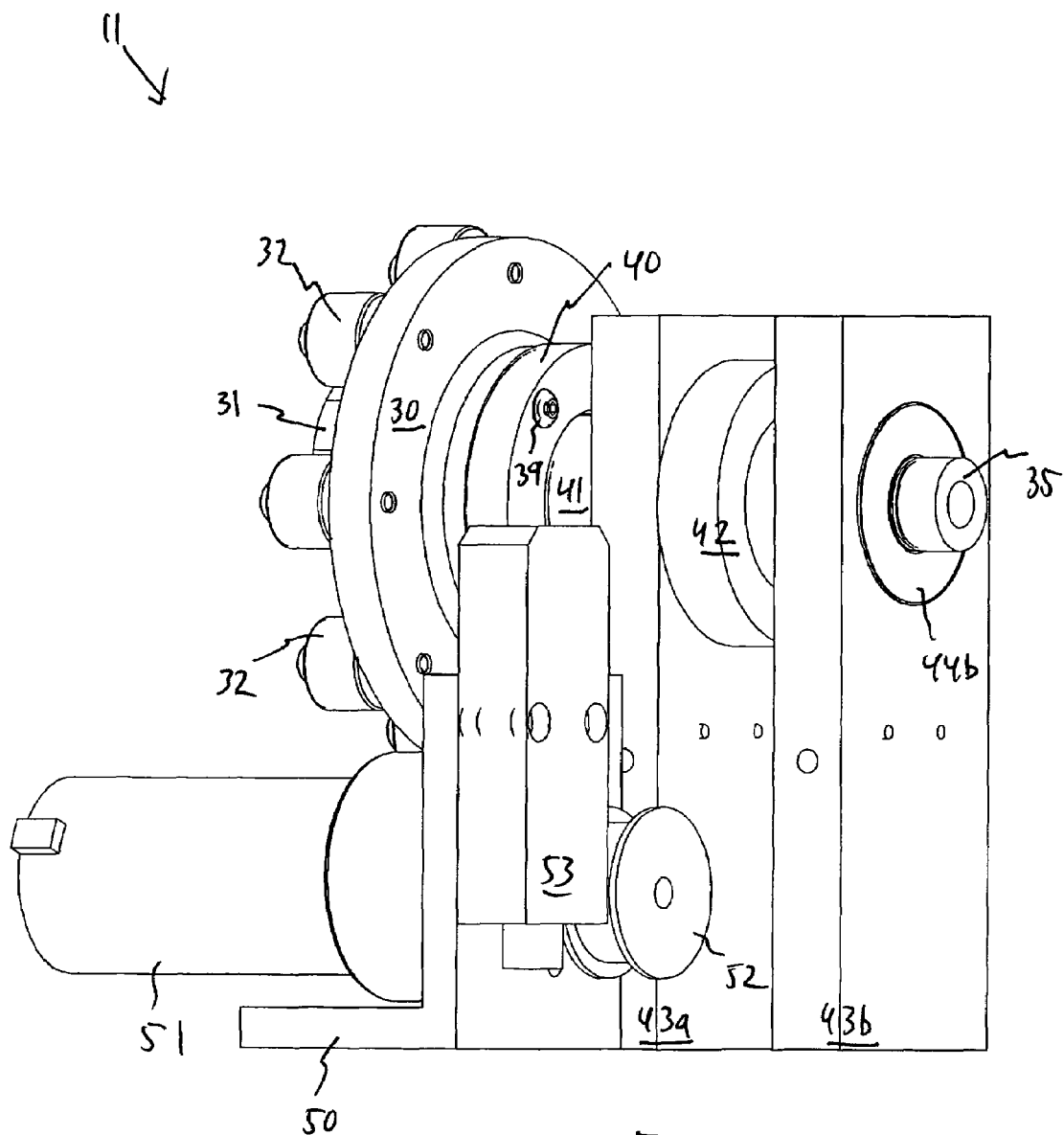
FIG. 5 is a perspective view from the rear right side of the swaging assembly.
Figure 6:
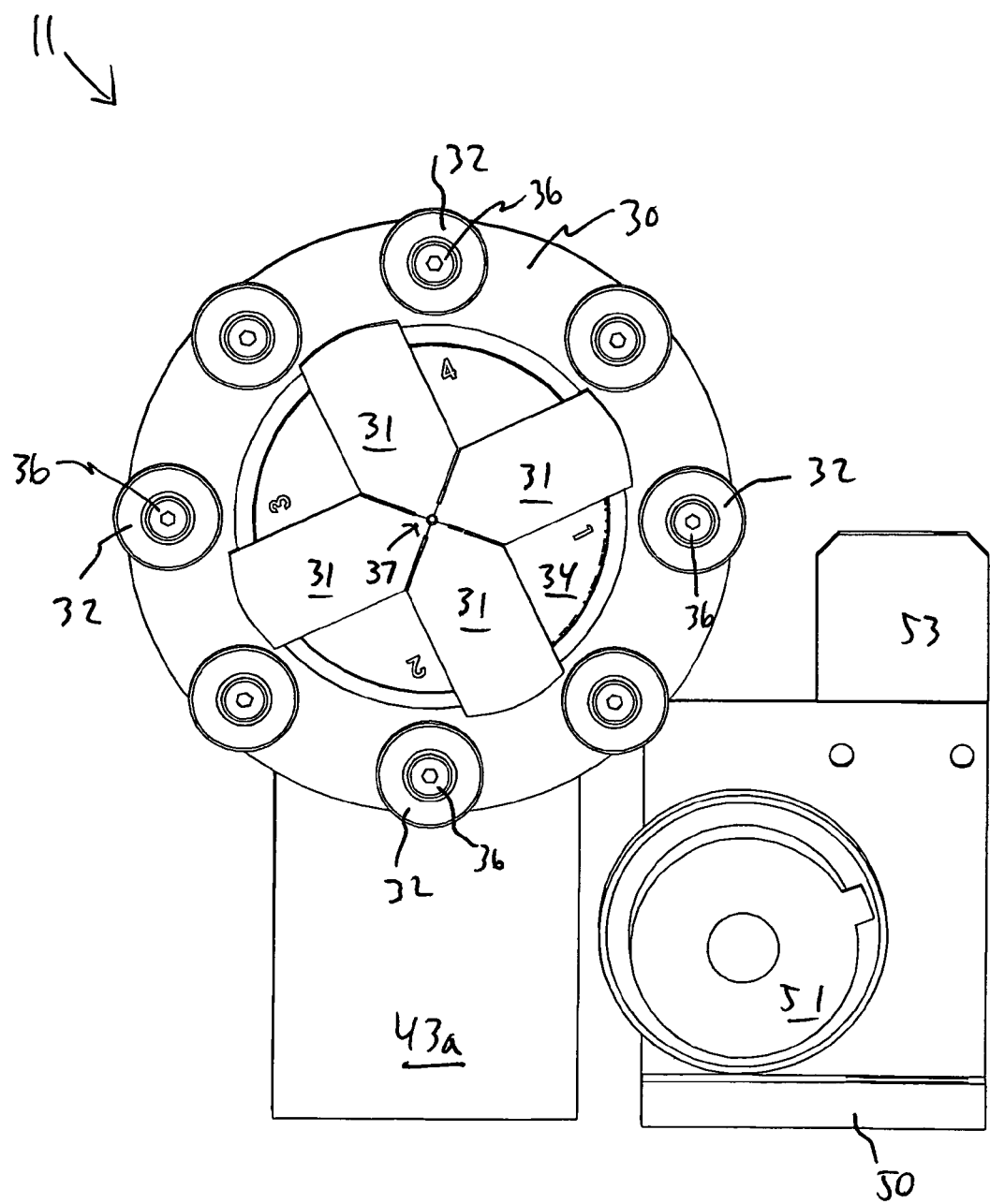
FIG. 6 is a front elevation view of the swaging assembly.
Figure 7:
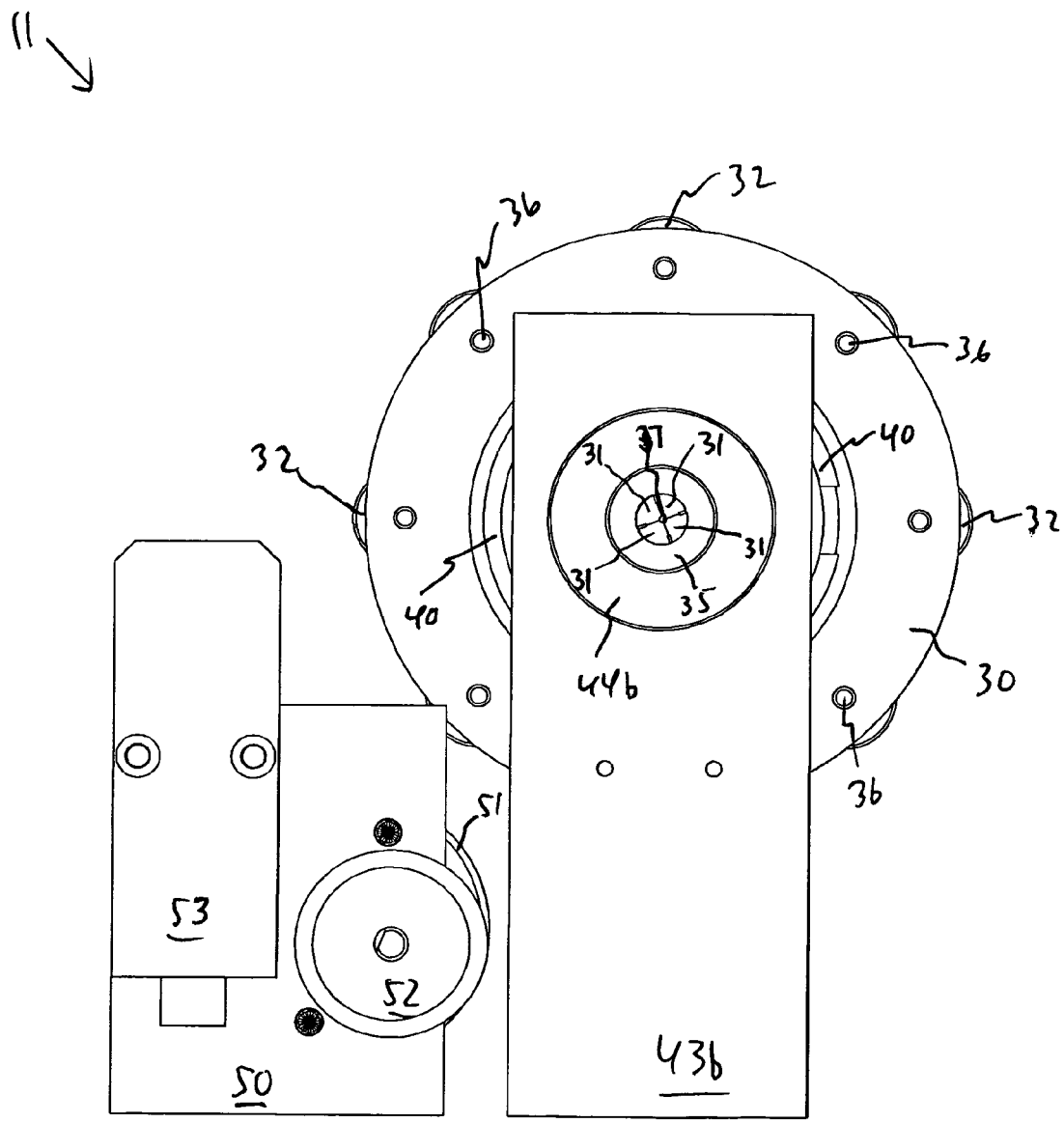
FIG. 7 is a rear elevation view of the swaging assembly.
Figure 8:
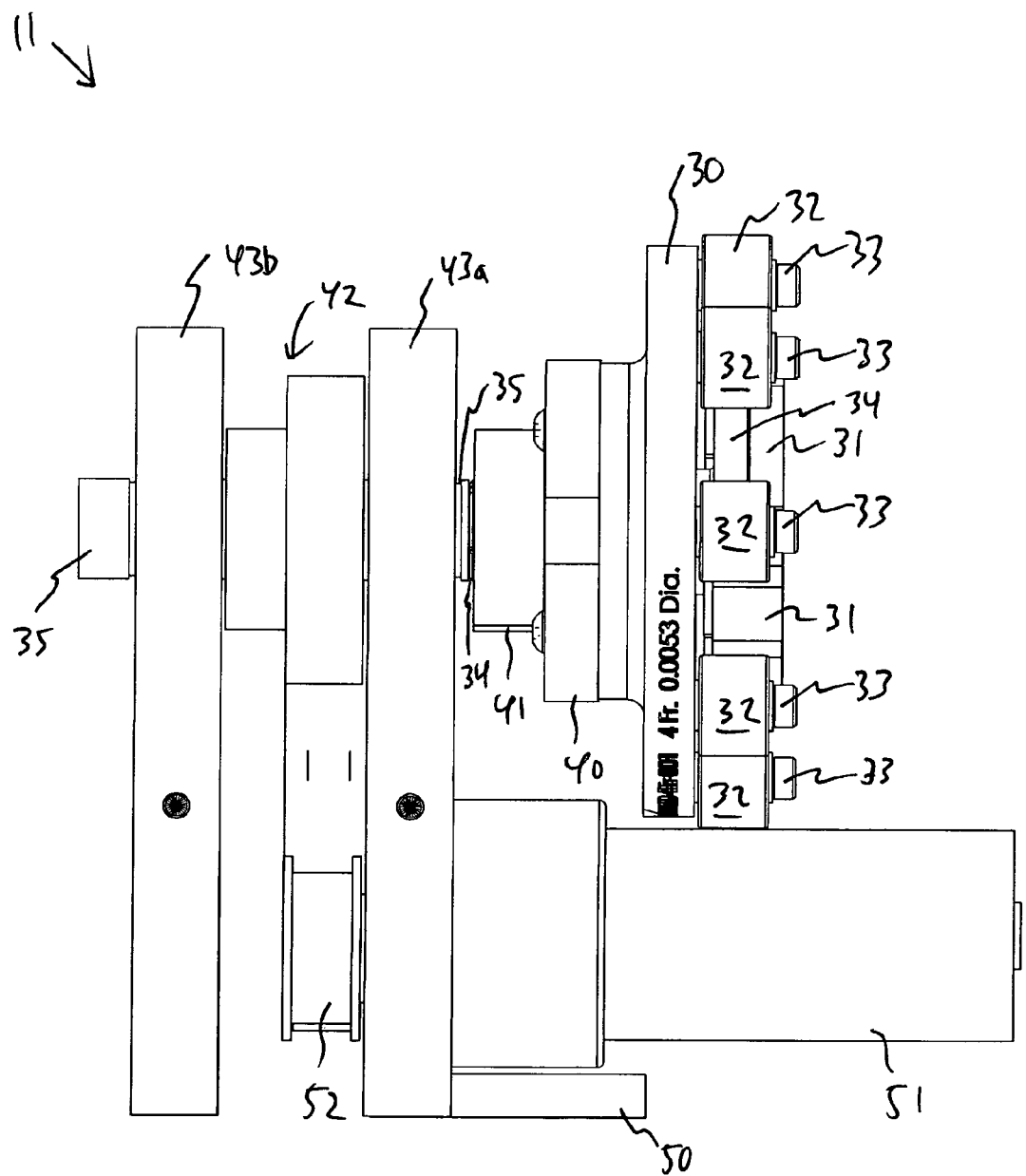
FIG. 8 is a left elevation view of the swaging assembly.
Figure 9:
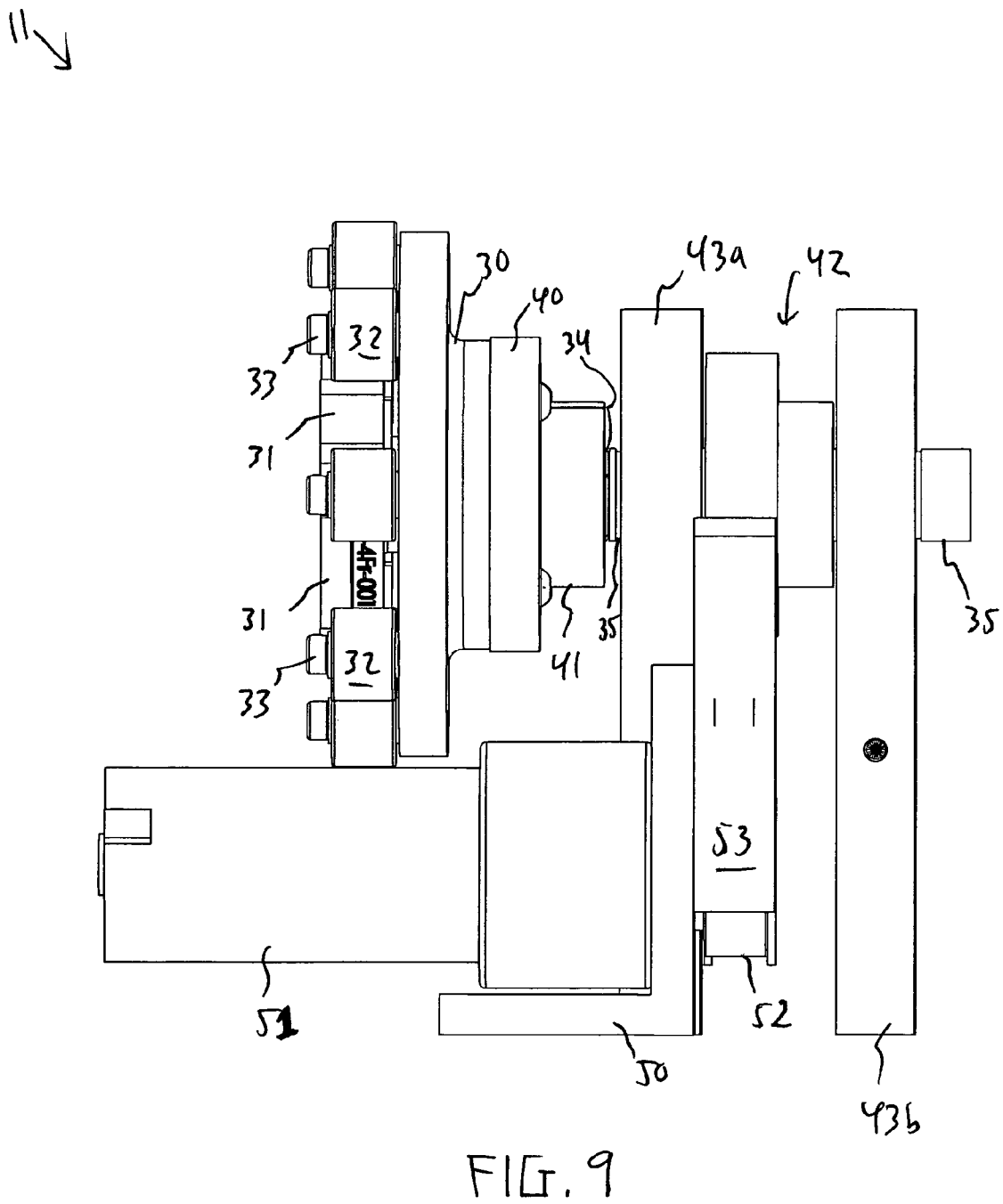
FIG. 9 is a right elevation view of the swaging assembly.
Figure 10:
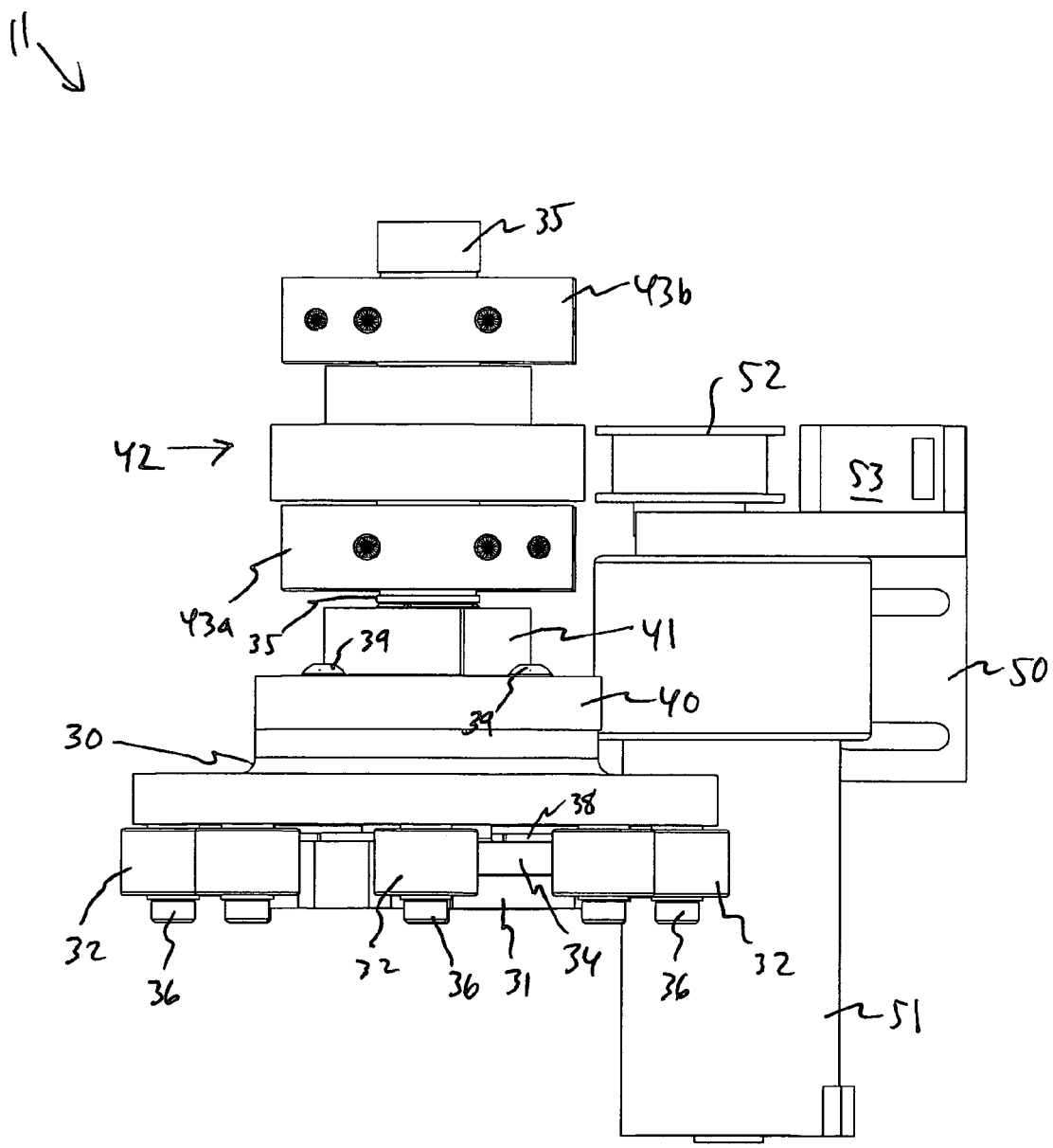
FIG. 10 is a top plan view of the swaging assembly.
Figure 11:
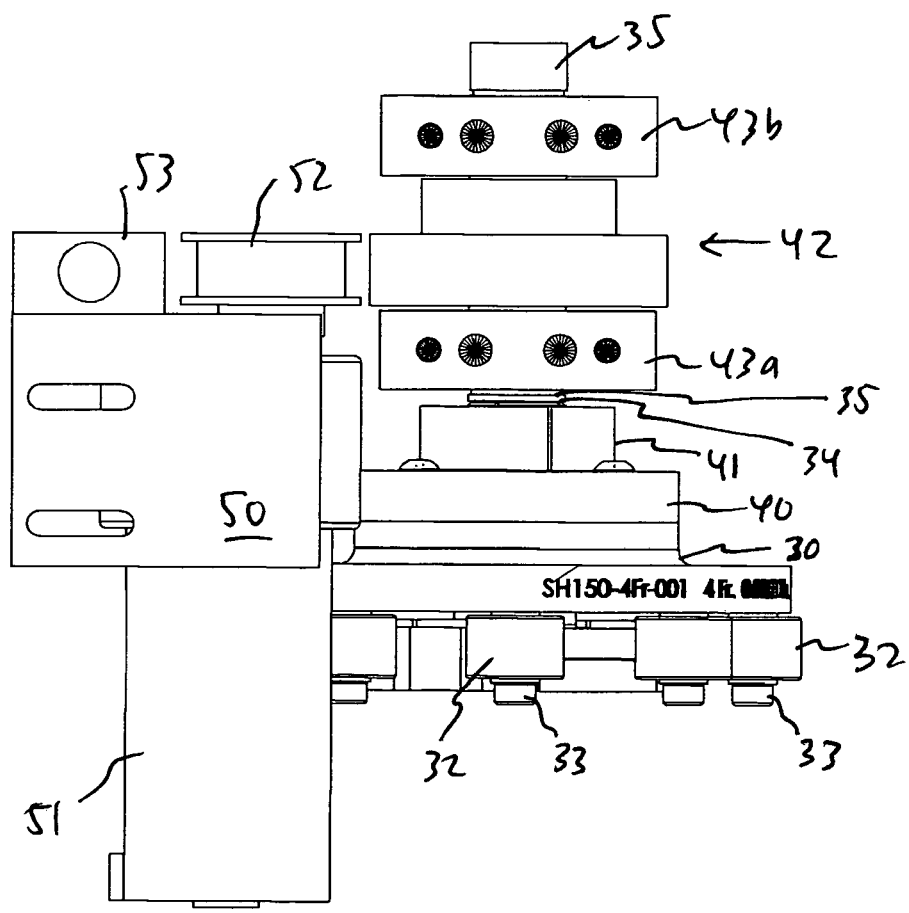
FIG. 11 is a bottom view of the swaging assembly.
Figure 12:
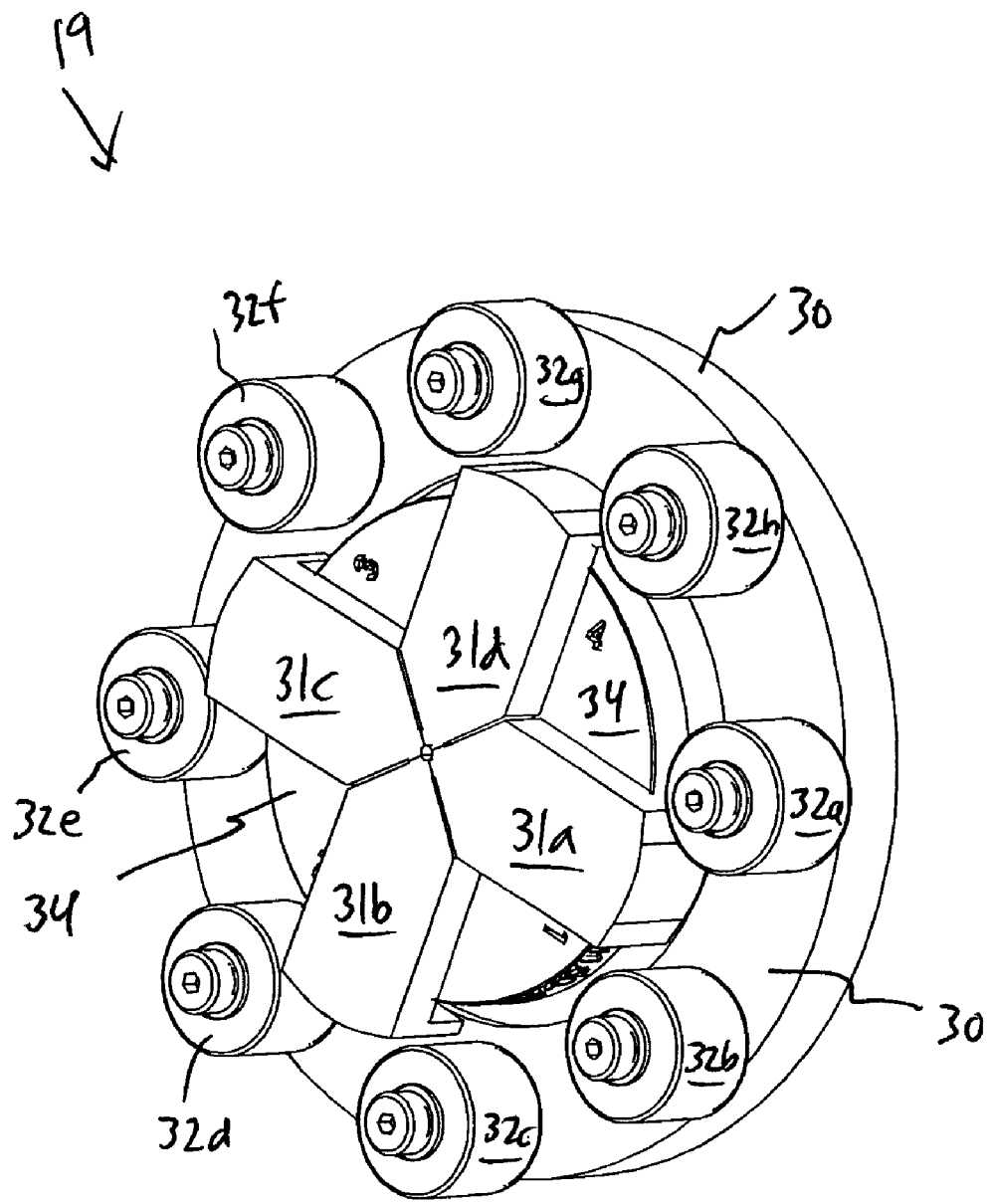
FIG. 12 is a perspective view from the front of an embodiment of a swaging head use in the swaging assembly.
Figure 13:
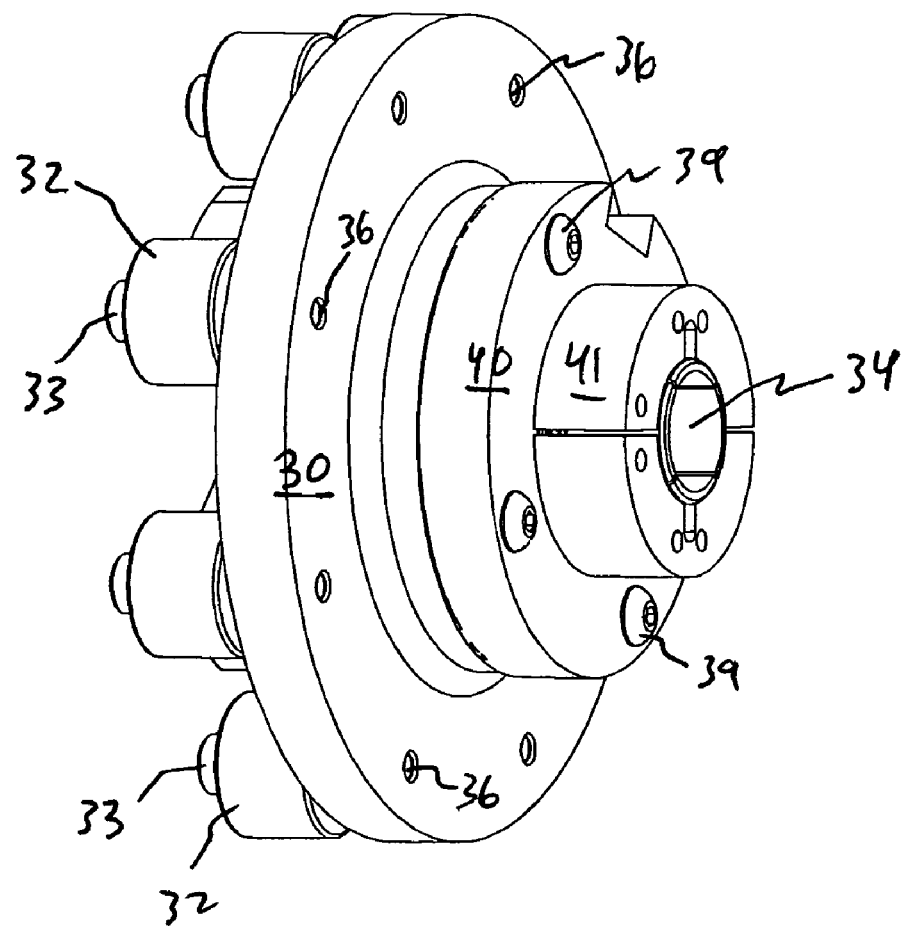
FIG. 13 is a perspective view from the rear of the swaging head.
Figure 14:
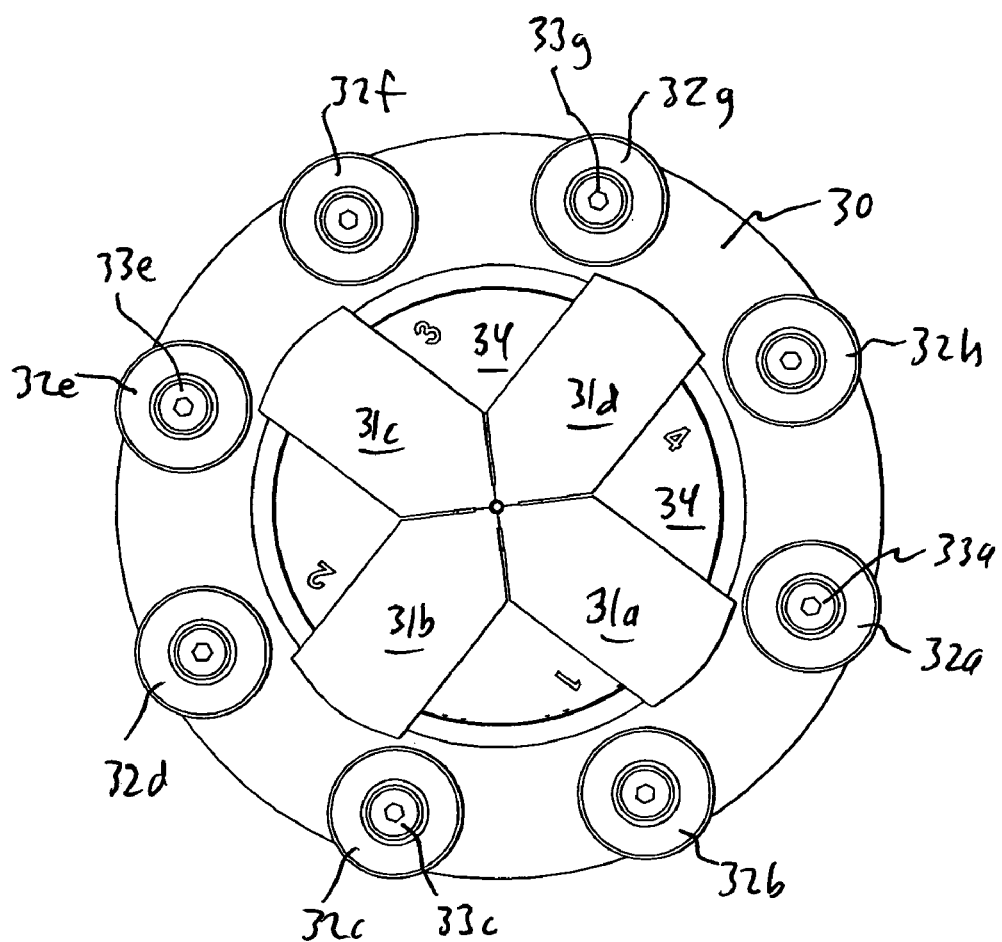
FIG. 14 is a front view of the swaging head.
Figure 15:
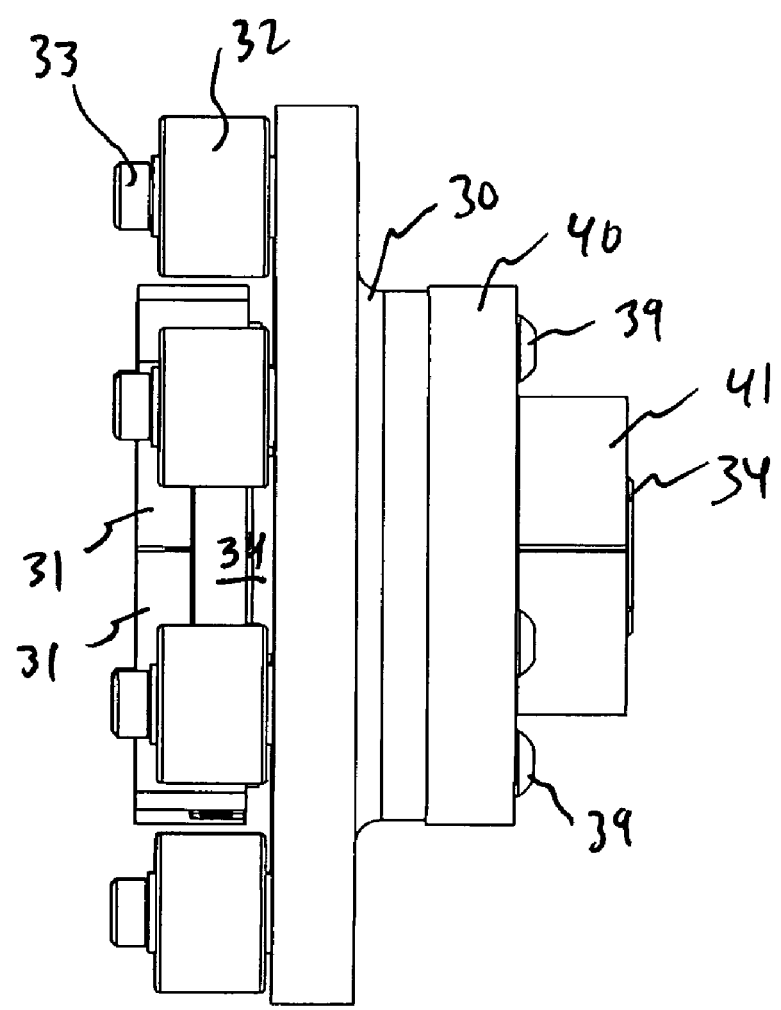
FIG. 15 is a side view of the swaging head.
Figure 16:
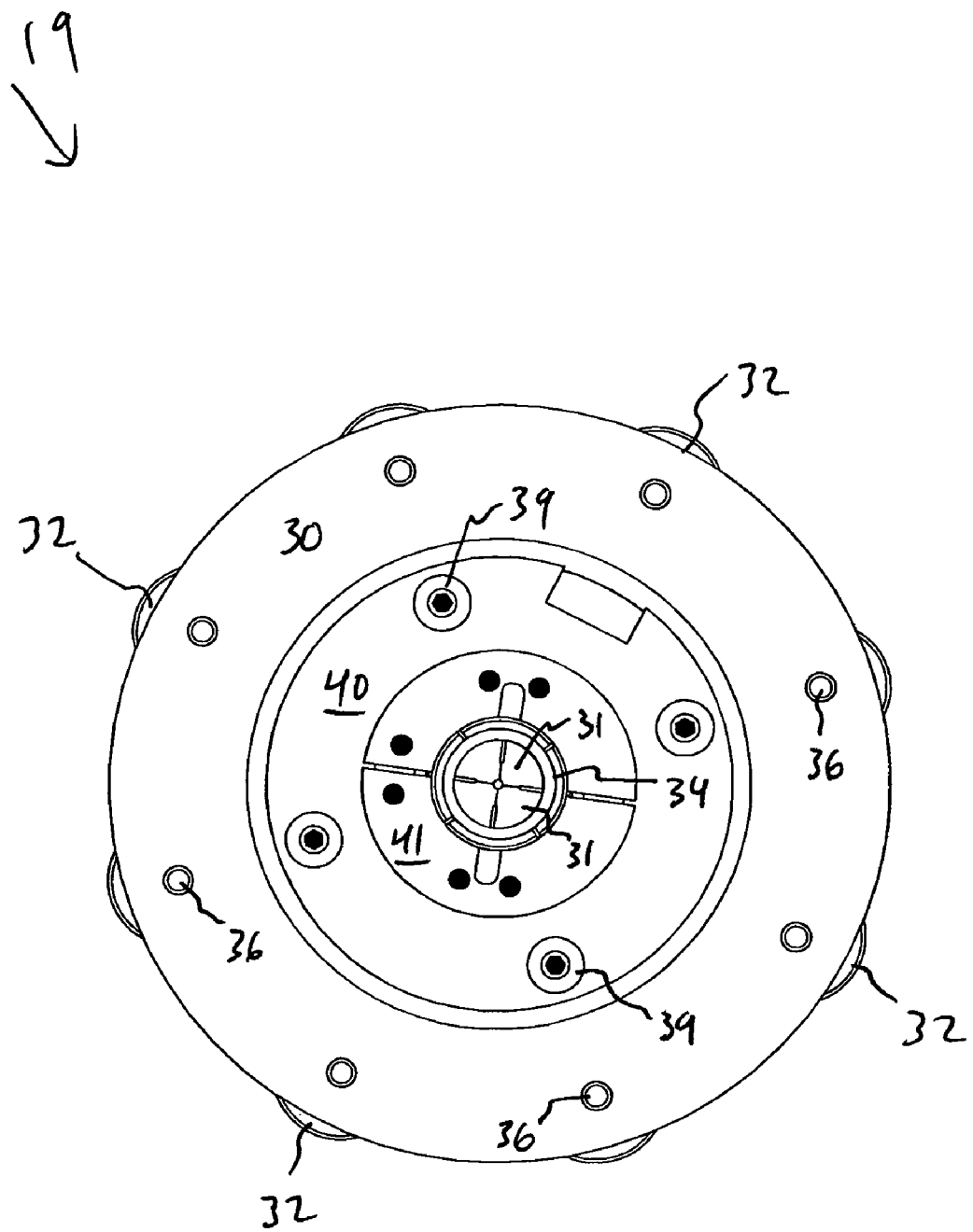
FIG. 16 is a rear view of the swaging head.

Referring to FIG. 1, a preferred embodiment of the swaging system of the present invention includes a swaging assembly 11, a drive mechanism 12, an infeed assembly 13, a base 14 and a safety cover 15. The swaging assembly 11 is disposed on the base 14, preferably slightly recessed with respect to it. The safety cover 15 preferably encloses swaging assembly 11 to prevent accidental contact with its moving parts by a user and to help keep in clean and free of dust, debris or the like. The infeed assembly 13 is disposed on top of the base and extends from the front end of the base 14 to the front face of the swaging assembly 11 through an opening in the cover 15. A product, products, article or material to be swaged, for example a medical catheter 16 is placed on the infeed assembly 13 and moved to the swaging assembly 11. The catheter 16 is processed by the assembly 11, for example marker bands are swaged onto the body of the catheter 16 and the processed product exits the opposite, back end of the swager 10. The catheter 16 is preferably manually controlled by the operator. However, it is within the purview of this invention that the catheter or other material processes may be automatically controlled by known materials handling, control and/or logging apparatus and methods.

FIGS. 2-11 show the swaging assembly 11 preferably constructed of a swage head 19, support elements described below, and the drive mechanism 12.

Referring also to FIGS. 12-17, the swage head 19 is constructed of a closer plate 30, a sliding bearing plate, slider plate 34, a plurality of swage elements 31a-b, a plurality of track rollers 23, and a main shaft 35. The closer plate 30 has a circular, preferably generally disc shaped configuration with a front face having predetermined recesses and a back face having an extension portion. The closer plate 30 also has a central aperture. The slider plate 34 has a disc shaped forward member of a predetermined diameter and thickness and a cylindrical hub member of a predetermined diameter and length extending rearwardly from the hub. The forward member of the slider plate 34 is disposed in a recess of the closer plate 30 and the rear hub member extends through the central aperture of the closer plate 30. The forward member of the slider plate 34 is shown to extend slightly outwardly from the front face of the closer plate. The slider plate 34 face preferably has predetermined radially configured slots 29 for retainers 38, which are coupled to the elements 31. In one embodiment, a retainer 38 is a flat plate structure secured to the rearward or back side of an element via a screw. The retainer 38 is configured to slide within the slider plate 34 slot 29. Alternatively, this structure may be reversed and the retainer may be fixed to the slider plate 34 and slide within a slot in the element 31. The closer plate 30 is preferably constructed of anodized aluminum, but may be constructed of other metal or rigid material or materials. The slider plate is preferably constructed of stainless steel, but may also be constructed of other rigid materials. Although the closer plate 30 and slider plate 34 are shown to have respective unitary structures, it within the purview of the invention that they may be constructed of plural parts.

Figure 18:
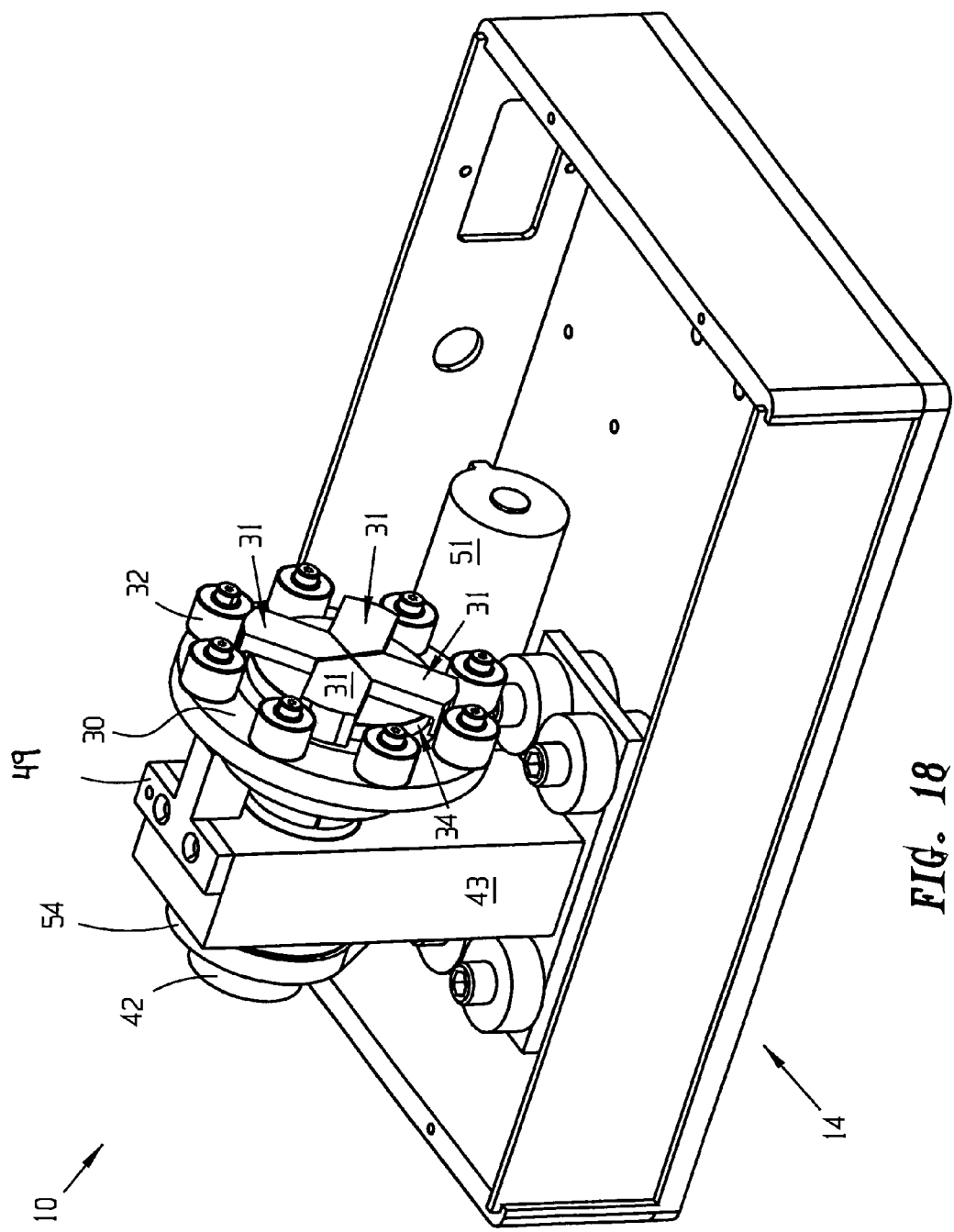
FIG. 18 illustrates a preferred embodiment of the swaging system wherein the swaging assembly is disposed in the base, and wherein the elements are shown in a closed position.
Figure 19:
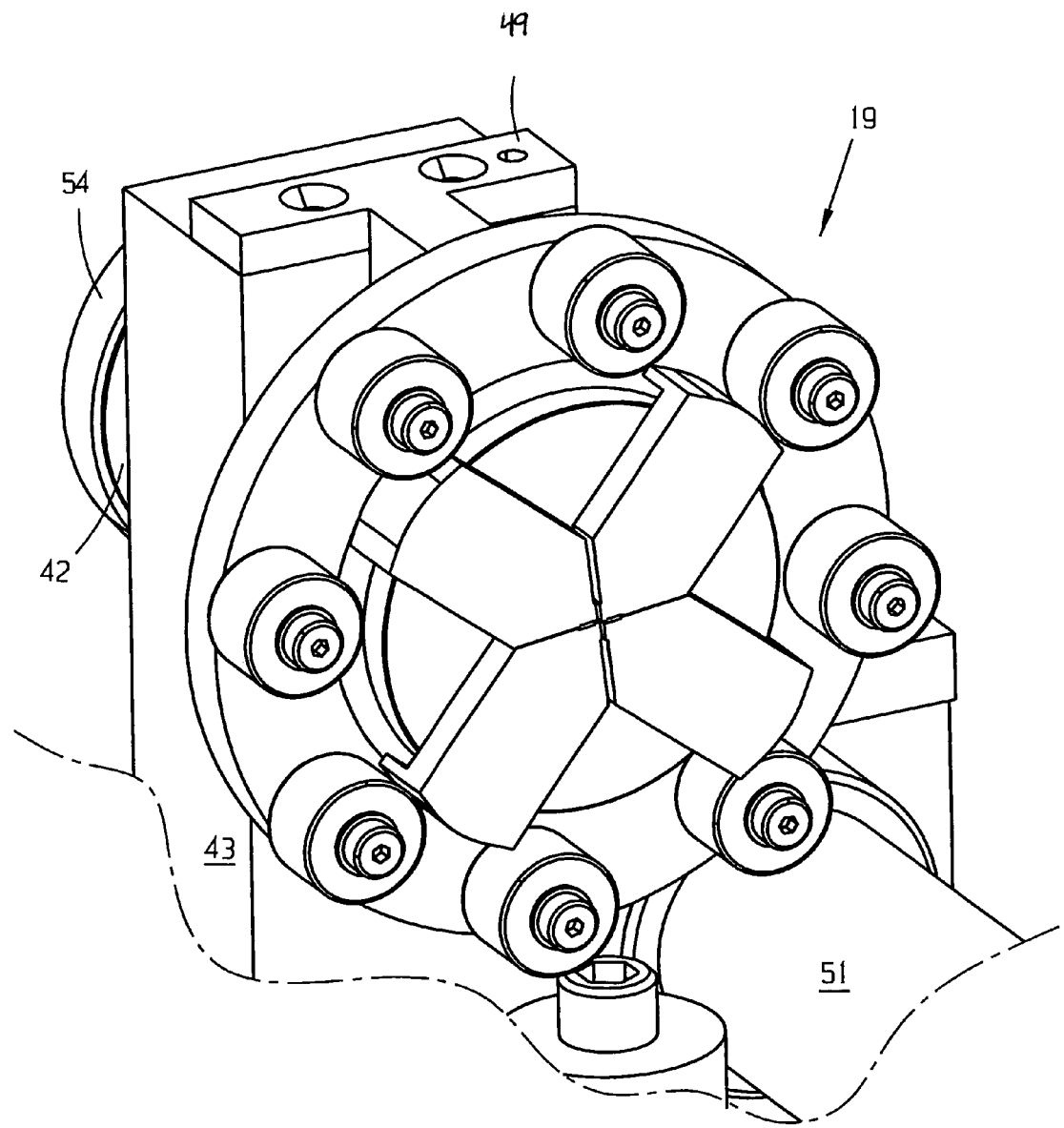
FIG. 19 illustrates the swaging assembly with the elements in an open position.

The closer plate 30 may be fixed in position as shown for example in FIGS. 18 and 19 by a rigid block 49 connection to the support 43. Alternatively, the closer plate 30 may be periodically rotated itself, for example by a belt connection of the clocking pulley 40 to an actuation mechanism. The rotation of the slider plate 34 may continue to be independent of the movement of the closer plate 30.

Figure 20:
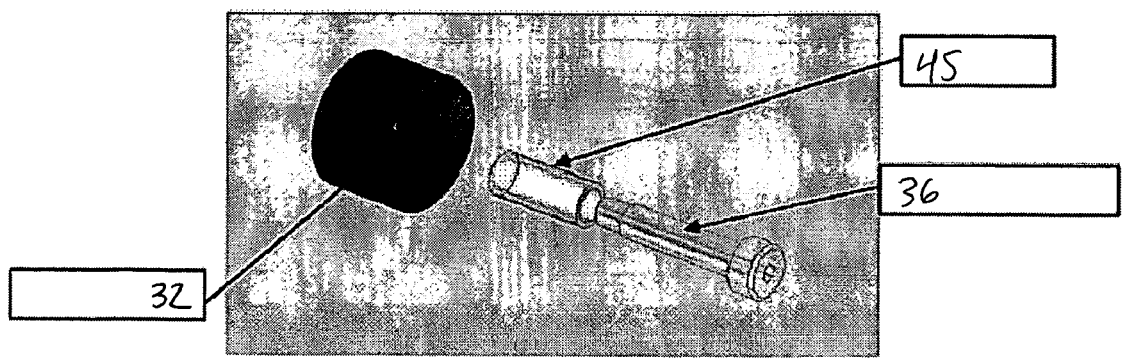
FIG. 20 is a perspective view of an embodiment of a track roller.

Track rollers 32 are rotatably connected to the front face of the closer plate 30 near its outer perimeter in a generally ring shaped pattern, each spaced a predetermined distance from one another. Referring also to FIG. 20., the track rollers 32 are connected to the closer plate 30 via screws 36 in plate 30 threaded apertures. Bushings 45 preferably separate the screws and rollers 32. The bushings 45 are preferably constructed of an elastomeric material of a predetermined Shore durometer characteristic related to the impact force to be imparted to the processed product during swaging. The rollers 32 have a predetermined diameter corresponding to the dimensions of the head 19 and the swaging elements 31. The number of rollers 32 is a function of the number of swaging elements 31. Although the head 19 is shown to have eight (8) rollers 32 it is within the purview of the invention to have as few as four rollers and as many as eighty rollers.

Figure 21:
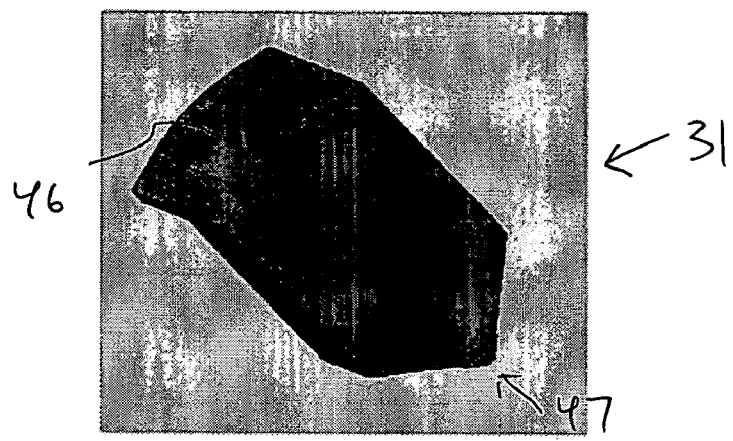
FIG. 21 is a perspective view of an embodiment of a swaging element.
Figure 22:
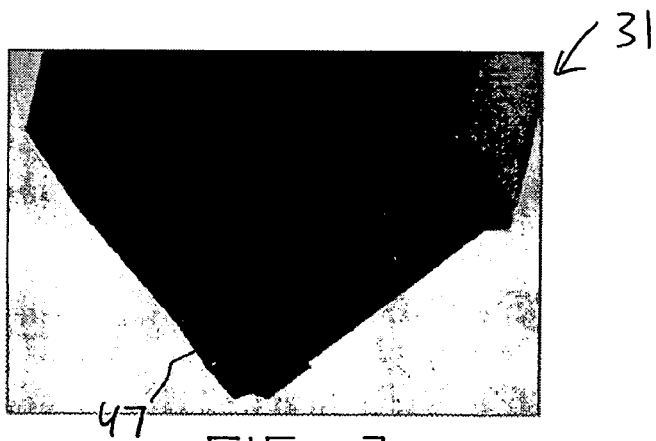
FIG. 22 is a perspective view of an embodiment of the distal end of the swaging element.

The swaging elements 31 are movably coupled to the slider plate 34 and arranged in a predetermined radial configuration surrounding a central aperture 37. The elements 31 move to open and close the aperture 37. The opening and closing diameter of the aperture is variable and is a function of the element 31 configuration and head 19 diameter. Referring also to FIGS. 21 and 22, the elements 31 have a predetermined configuration with an outward or proximal end 46, substantially straight side faces, and an angled inward or distal end 47. The proximal ends 46 have a substantially curved cam profile face and the distal ends preferably have a shaped contact surface or profile. The thickness or depth of the elements 31 is variable depending upon the width or thickness of the product to be swaged. The swaging elements 31 are slidably coupled to the slide plate, preferably via retainers 38 coupled to the rearward or back side of the elements 31. In the preferred embodiment shown, the swaging elements 31 are constructed of electro-polished stainless steel. However, the composition of the elements 31 is variable and can be rigid or semi rigid depending upon the product or material being impacted during swaging. The number of elements 31 is related to the product being processed and the desired swaging profile. Although the head 19 is shown to have four (4) elements 31 it is within the purview of the invention to have as few as two elements and as many as forty elements.

Referring again to FIGS. 2-11, the main shaft 35 is preferably supported by a pair shaft supports 43 *a* and *b* which are connected to the base 14 and separated a predetermined distance. Bearings 44 *a* and *b* are fixedly disposed in aligned apertures in the supports 43. The shaft 35 is disposed through the bearings 44. The shaft 35 is shown to extend out the back end of support 43*b*. Main shaft pulley 42 is connected to the shaft 35 and disposed between the supports 43. Referring also to FIGS. 18 and 19, drive belt 45 is coupled to the main shaft pulley 42 to drivably couple the motor 51 (via drive pulley 52) to the main shaft 35. Main shaft collar 41 is disposed around and connects slider hub 34 and shaft 35 forward of support 43*a*. Clocking pulley 40 is disposed around shaft 35 and is fixedly connected to the rearward side of the closing plate 30, preferably via screws 39. Rotating element bearing 48 is coupled to plate 30. Slider plate 34 hub extends through the bearing 48. These structures cooperate to mount the head 19 in position for swaging and to rotatably couple the slider plate 34 with respect to the closer plate 30.

Referring again to FIGS. 2-11, and to FIGS. 18 and 19, the drive mechanism 12 preferably includes a drive motor 51 connected to the base 14 via motor mount 50, a rotatable drive pulley 52 connected to the motor 51, and an electronic control assembly 53. In the preferred embodiment shown, the motor 51 is preferably a Pittman GM Gearmotor. However, other drive motors may be substituted therefor. The control assembly 53 is preferably a 110V/220V 50/60 Hz system. Drive belt 54 extends from the drive pulley 52 to the shaft pulley 42 so that operation of the motor 51 drives the head 19 as detailed herein. The motor 51 can be actuated in a variety of profiles to provide a variety of rotations less than or equal to 360 degrees, and either continuous motion or oscillating motion, for example in 10 degree increments. Further the speed and direction of motion can be varied as desired depending upon the swaging application. The motor control 53 is preferably communicatively connected to a foot pedal control, not shown.

Figure 17:
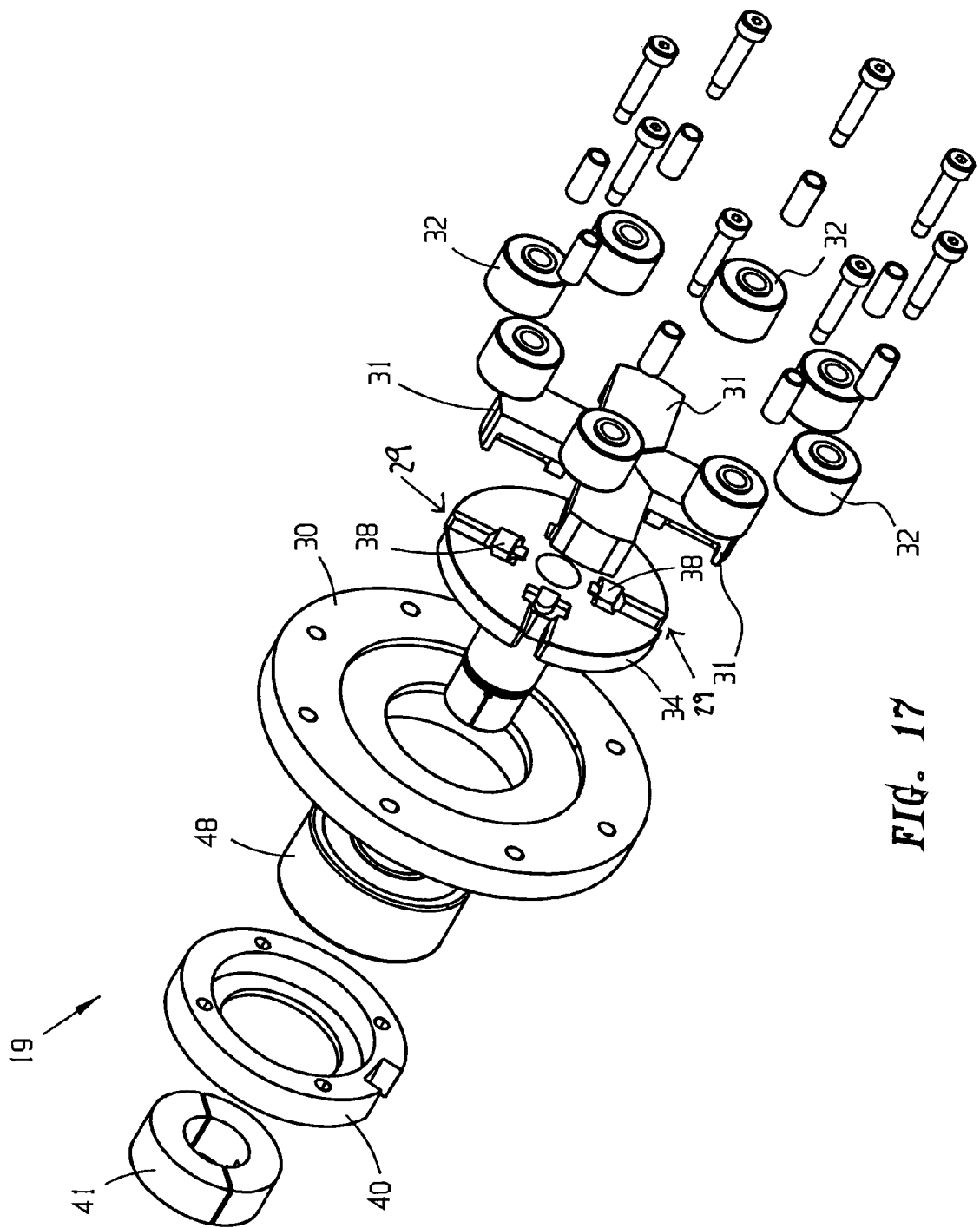
FIG. 17 is an exploded view of an embodiment of the swaging head.

Referring again to FIGS. 2-22, in operation, the swage elements 31 are carried on the sliding bearing plate or slider plate 34. The slider plate 34 is attached to the closer plate 30 via a rotating element bearing 48. The slider plate 34 is rotated with respect to the closer plate 30, and the track rollers 32 attached to the closer plate 30 contact the swage elements 31, resulting in rapid linear closing of the swage elements 31 while the elements are simultaneously being rotated. The closing of the swage elements 31 onto the product, for example a medical product such as marker bands (not shown) positioned on a catheter 16, being processed imparts a radial compression force on the product 16 resulting in a desired diameter reduction. The amount of diameter reduction and the final diameter of the product being processed is determined by a profile cut into the distal end of each swage element 31. FIG. 17 shows an exploded view of an embodiment of the swage head assembly 19. The slider plate 34 is attached to the closer plate 30 via the rolling element bearing 48. Each swage element 31 is secured to the slider plate 34 preferably by a round flat plate and screw. The entire assembly 19 is mounted to a machine base 14 via the shaft 35. As is best shown in FIGS. 21 and 22, each swage element 31 has the proximal contact surface 46 for the track roller 32 and a distal swage profile 47 used to process the product 16. The swage profile 47 is designed to generate a gradual reduction in the product diameter, resulting in lower hoop stresses on the processed product and material. This reduces the chance of product damage.

FIG. 18 shows the swage elements 31 in the open position. The swage elements 31 are moved to this open position through the inertia imparted on each element 31 through the rotation of the slider plate 34 or alternatively via a compression spring. FIG. 19 shows the swage elements 31 in the closed position. The curved surface of the proximal or outward end of each swage element 31 contact the track rollers 32 and imparts a smooth but rapid movement of the element 31 from an open to a closed position. The contact force between the track rollers 32 and swage elements 31 is managed through the use of the bushing 45 on the mounting screw 36 of each track roller 32 as is shown in FIG. 20. The bushing 45 provides for relative movement between the track roller 32 and the swage element 31. This relative movement achieves, among other benefits, the following:

1) consistent swage force transferred to each swage element 31;
2) compensation for variations in the location of each track roller 32 with respect to each swage element 31; and 3) dampening of vibrations generated by the impact of the track rollers 32 with the swage elements 31, resulting in lower machine noise.

Figure 23:
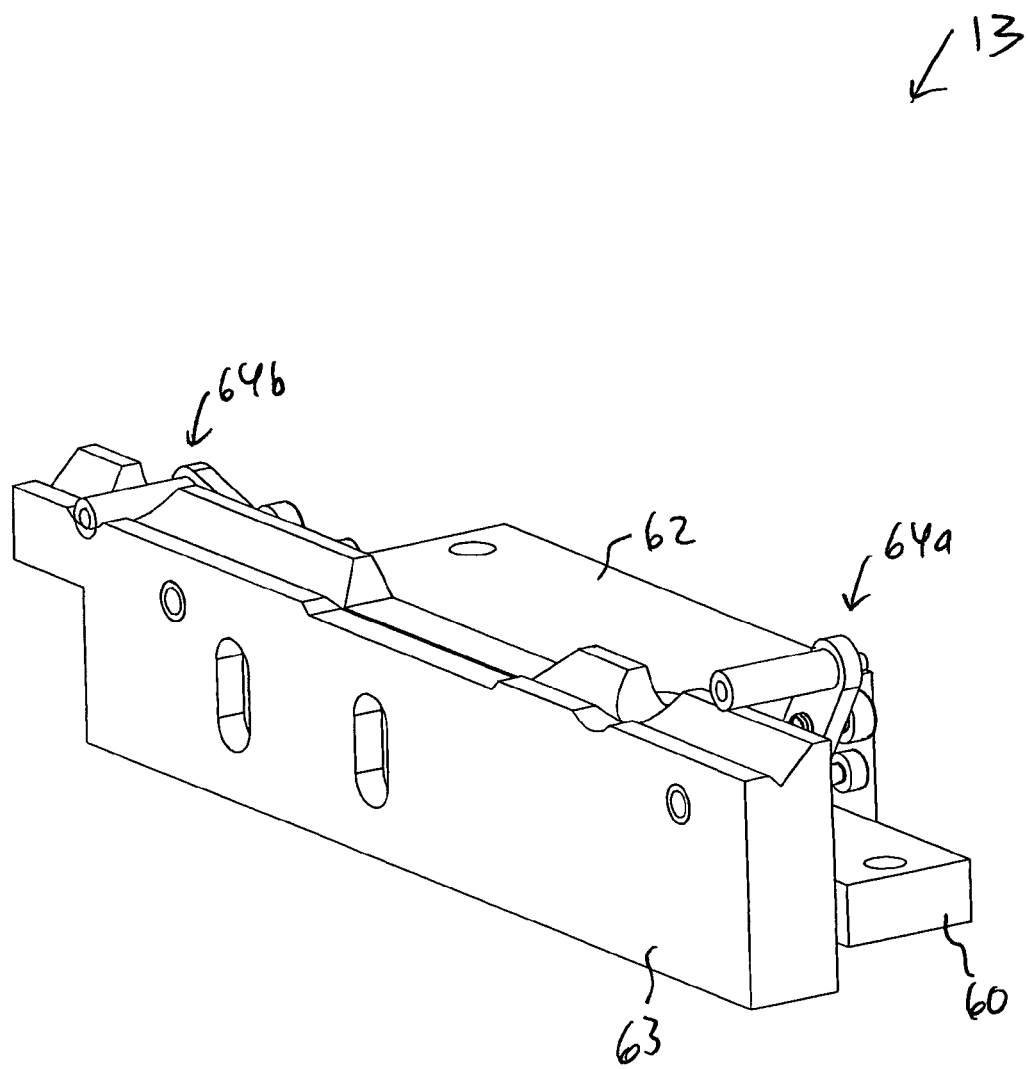
FIG. 23 is a perspective view from the left front of an embodiment of an infeed assembly used in the swaging system.
Figure 24:
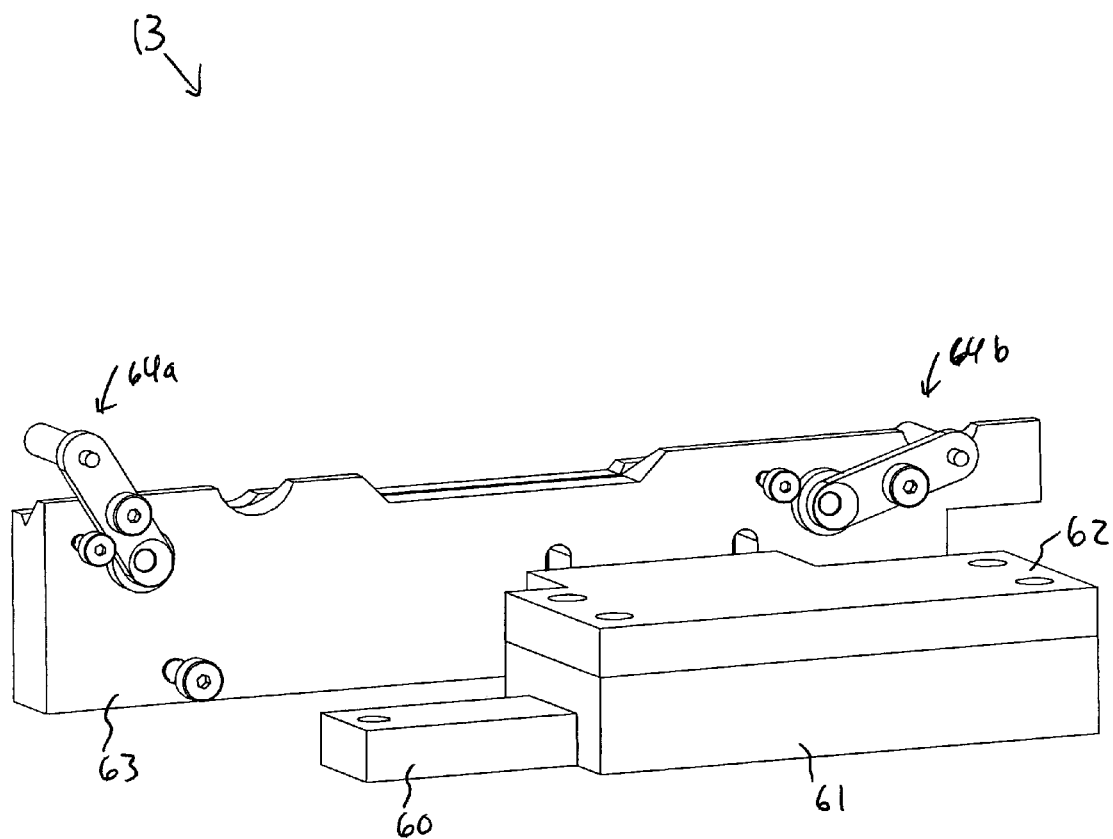
FIG. 24 is a perspective view from the right side of the infeed assembly.
Figure 25:
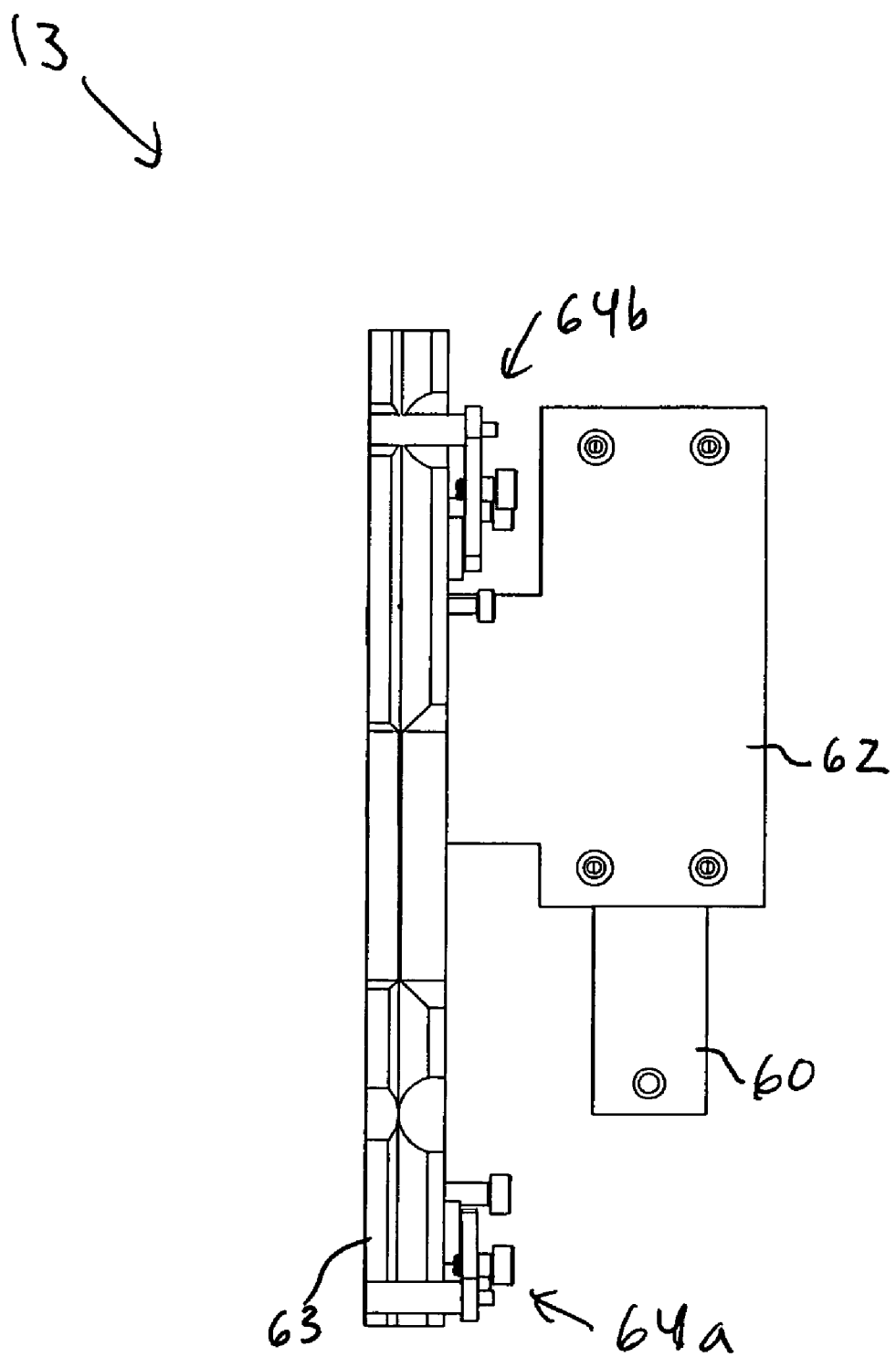
FIG. 25 is a top plan view of the infeed assembly.

FIGS. 23, 24 and 25 show a preferred embodiment of the infeed assembly including a slide base, 60, slide carriage 61, a Vee block holder 62, an infeed Vee block 63 of a predetermined length and having an alignment groove on its top surface, and a pair of infeed clamps 64 *a* and *b* disposed at predetermined locations with respect to the Vee block.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A swage head comprising a first plate, a second plate rotatable with respect to the first plate about an axis, said second plate having a radially extending face, a plurality of swage elements slidably coupled to the second plate and having a swaging profile adapted to contact a product to be swaged and each swage element having a cam profile, and a plurality of slide rollers rotatably connected to the first plate and adapted to contact the cam profiles of the swage elements, wherein the swage elements are slidably connected to the second plate via retainers, each retainer axially extending from each swage element so that each swage element circumferentially overlaps the face of the second plate.

2. The swage head of claim 1, wherein the first plate is a closer plate and the second plate is a slider plate, and wherein the closer plate and slider plate are rotatably coupled by a bearing.

3. The swage head of claim 1, wherein the first plate is stationary and the second plate is rotationally driven.

4. The swage head of claim 1, wherein the first and second plates have a circular structure.

5. The swage head of claim 1, wherein the swage elements move linearly with respect to the second plate.

6. The swage head of claim 1, wherein there are two slide rollers for every swage element.

7. The swage head of claim 1, wherein there are at least four swage elements.

8. The swage head of claim 1, wherein the swage elements are disposed so that their swaging profiles surround an aligned central aperture in the first plate and second plate, the central aperture adapted for positioning an article to be swaged, whereby rotation of the second plate moves the swage elements into contact with the slide rollers and causes them to periodically move radially into contact with the article and then away from contact.

9. The swage head of claim 5 wherein there are four swage elements disposed around the central aperture.

10. The swage head of claim 1, wherein the first plate is a disc shaped closer plate with a central aperture and the second plate is a rotationally driven slider plate with a disc member and a cylindrical hub member extending from the disc member, and wherein the slider plate has a central aperture aligned with the central aperture of the closer plate, and wherein the closer plate and slider plate are rotatably coupled by a bearing, wherein there are at least four swage elements and the retainers are disposed in slots in the slider plate, wherein the swage elements move linearly with respect to the slider plate, wherein there are two slide rollers for each swage elements and the slide rollers are disposed near the circumferential periphery of the closer plate, and wherein the swage elements are disposed so that their swaging profiles surround an aligned central apertures of the closer plate and slider plate, the central aperture adapted for positioning an article to be swaged and impacted by the swage elements, whereby rotation of the second plate moves the swage elements into contact with the slide rollers and causes them to periodically move radially into contact with the article and then away from contact.

11. A swaging assembly, comprising:
 a. a swage head comprising a first plate, a second plate rotatable with respect to the first plate about an axis, said second plate having a radially extending face, a plurality of swage elements slidably coupled to the second plate via retainers which are slidably disposed in slots in the second plate, the swage elements having a swaging profile adapted to contact a product to be swaged and each swage element having a cam profile, and a plurality of slide rollers rotatably connected to the first plate and adapted to contact the cam profiles of the swage elements, each retainer axially extending from each swage element so that each swage element circumferentially overlaps the face of the second plate;
 b. a mount supporting the swage head; and
 c. a drive actuating the swage head and rotating the second plate.

12. The swaging assembly of claim 11, wherein the first plate is a disc shaped closer plate with a central aperture and the second plate is a rotationally driven slider plate with a disc member and a cylindrical hub member extending from the disc member, and wherein the slider plate has a central aperture aligned with the central aperture of the closer plate, and wherein the closer plate and slider plate are rotatably coupled by a bearing, wherein there are at least four swage elements, wherein the swage elements move linearly with respect to the slider plate, wherein there are two slide rollers for each swage elements and the slide rollers are disposed near the circumferential periphery of the closer plate, and wherein the swage elements are disposed so that their swaging profiles surround an aligned central apertures of the closer plate and slider plate, the central aperture adapted for positioning an article to be swaged and impacted by the swage elements, whereby rotation of the second plate moves the swage elements into contact with the slide rollers and causes them to periodically move radially into contact with the article and then away from contact.

13. The swaging assembly of claim 11, wherein the mount comprises at least one support communicatively coupled to the first plate.

14. The swaging assembly of claim 11, wherein the mount holds the first plate stationary.

15. The swaging assembly of claim 11, wherein the mount permits rotational movement of the first plate.

16. The swaging assembly of claim 11, wherein the drive comprises an electric motor and at least one pulley and belt communicatively coupling the motor to the second plate.

17. A swaging system for swaging an article, comprising:
  a. a swaging assembly, comprising:
    i. a swage head comprising a first plate, a second plate rotatable with respect to the first plate about an axis, said second plate having a radially extending face, a plurality of swage elements slidably coupled to the second plate via retainers which are slidably disposed in slots in the second plate, each retainer axially extending from each swage element so that each swage element circumferentially overlaps the face of the second plate, the swage elements having a swaging profile adapted to contact a product to be swage and each swage element having a cam profile, and a plurality of slide rollers rotatably connected to the first plate and adapted to contact the cam profiles of the swage elements;
    ii. a mount supporting the swage head; and
    iii. a drive actuating the swage head and rotating the second plate; and
  b. an article input assembly for orienting an article for swaging with respect to the swaging assembly.

18. The swaging system of claim 17, wherein:
  c. with respect to the swaging assembly, wherein the first plate is a disc shaped closer plate with a central aperture and the second plate is a rotationally driven slider plate with a disc member and a cylindrical hub member extending from the disc member, and wherein the slider plate has a central aperture aligned with the central aperture of the closer plate, and wherein the closer plate and slider plate are rotatably coupled by a bearing, wherein there are at least four swage elements, wherein the swage elements move linearly with respect to the slider plate, wherein there are two slide rollers for each swage elements and the slide rollers are disposed near the circumferential periphery of the closer plate, and wherein the swage elements are disposed so that their swaging profiles surround an aligned central apertures of the closer plate and slider plate, the central aperture adapted for positioning an article to be swaged and impacted by the swage elements, whereby rotation of the second plate moves the swage elements into contact with the slide rollers and causes them to periodically move radially into contact with the article and then away from contact;
  d. with respect to the mount, the mount comprises at least one support communicatively coupled to the first plate; and
  e. with respect to the drive, wherein the drive comprises an electric motor and at least one pulley and belt communicatively coupling the motor to the second plate.

19. The swaging assembly of claim 18, wherein the input assembly comprises a support block for supporting and guiding the article to the swaging assembly and at least one clamp for securing the article with respect to the support block.

* * * * *